United States Patent
Heinrich et al.

(10) Patent No.: US 12,378,225 B2
(45) Date of Patent: Aug. 5, 2025

(54) PROCESS FOR MANUFACTURING (S)-3-HYDROXY-1-(1H-INDOL-5-YL)-2-OXO-PYRROLIDINE-3-CARBOXYLIC ACID 3,5-DIFLUORO-BENZYLAMIDE

(71) Applicant: Merck Patent GmbH, Darmstadt (DE)

(72) Inventors: Timo Heinrich, Freigericht (DE); Jeyaprakashnarayanan Seenisamy, Bangalore (IN)

(73) Assignee: Merck Patent GmbH, Darmstadt (DE)

( * ) Notice: Subject to any disclaimer, the term of this patent is extended or adjusted under 35 U.S.C. 154(b) by 764 days.

(21) Appl. No.: 17/597,102

(22) PCT Filed: Jun. 30, 2020

(86) PCT No.: PCT/EP2020/068317
§ 371 (c)(1),
(2) Date: Dec. 27, 2021

(87) PCT Pub. No.: WO2021/001328
PCT Pub. Date: Jan. 7, 2021

(65) Prior Publication Data
US 2022/0251072 A1    Aug. 11, 2022

(30) Foreign Application Priority Data
Jul. 3, 2019 (EP) .................................... 19184056

(51) Int. Cl.
*C07D 403/04* (2006.01)
(52) U.S. Cl.
CPC .................................. *C07D 403/04* (2013.01)
(58) Field of Classification Search
CPC .................................................. C07D 403/04
See application file for complete search history.

(56) References Cited

U.S. PATENT DOCUMENTS

| | | |
|---|---|---|
| 8,895,535 B2 | 11/2014 | Heinrich et al. |
| 9,796,709 B2 | 10/2017 | Kobayashi et al. |
| 10,005,756 B2 | 6/2018 | Heinrich et al. |
| 10,093,623 B2 | 10/2018 | Heinrich et al. |
| 2013/0296274 A1 | 11/2013 | Heinrich et al. |
| 2015/0031670 A1 | 1/2015 | Heinrich et al. |
| 2015/0376199 A1 | 12/2015 | Chen et al. |
| 2017/0088508 A1 | 3/2017 | Hughes et al. |
| 2017/0196841 A1 | 7/2017 | Fleury et al. |
| 2017/0226080 A1 | 8/2017 | Heinrich et al. |

FOREIGN PATENT DOCUMENTS

| | | |
|---|---|---|
| CN | 104245675 | 12/2014 |
| CN | 106660989 | 5/2017 |
| CN | 107250119 | 10/2017 |
| CN | 107257785 | 10/2017 |
| JP | 2013-544781 A | 12/2013 |
| JP | 2015-512426 A | 4/2015 |
| JP | 2016-513091 A | 5/2016 |
| JP | 2017-523995 A | 8/2017 |
| WO | 2012/048775 | 4/2012 |
| WO | 2013/149704 | 10/2013 |
| WO | 2015/087994 A1 | 6/2015 |
| WO | 2016/020031 | 2/2016 |

OTHER PUBLICATIONS

Dale L. Boger and Hamideh Zarrinmayeh, J. Org. Chem. 1990, 55, 1379-1390.*
Han et al., "Recent development of peptide coupling reagents in organic synthesis", Science Direct, Tetrahedron 60, 2004, pp. 2447-2467.
International Search Report issued Sep. 15, 2020 in PCT/EP2020/068317, 4 pages.
Written Opinion issued Sep. 15, 2020 in PCT/EP2020/068317, 6 pages.
Heinrich et al., "A Clinical Compound for the Treatment of Cancer", Journal of Medicinal Chemistry, vol. 62, No. 24, 2019, pp. 11119-11134.
Website https://pubchem.ncbi.nlm.nih.gov/compound/15450145 : 5 Chemical Vendors, printed on Jun. 13, 2024, National Library of Medicine, PubChem CID 15450145, 5 Chemical Vendors, 15 pages.
Website https://pubchem.ncbi.nlm.nih.gov/compound/154501 45: 5 Chemical Vendors, printed on Jun. 7, 2024, National Library of Medicine, PubChem CID 154501, 5 Chemical Vendors, 10 pages.
Taiwanese Office Action dated Mar. 6, 2024, in Taiwanese Application No. 109122384, 9 pages.
Chinese Office Action dated Oct. 16, 2023, in Chinese Application No. 202080048299.1, with English translation 16 pages.
Davis et al., "Asymmetric Hydroxylation of Enolates with N-Sulfonyloxaziridines", Chem. Rev., vol. 92, No. 5, Feb. 6, 1992, pp. 919-934.
Office Action received for Japanese Patent Application No. 2022-500028, mailed on Jun. 14, 2024, 6 pages with English translation.

* cited by examiner

*Primary Examiner* — Rebecca L Anderson
(74) *Attorney, Agent, or Firm* — Grüneberg and Myers PLLC

(57) ABSTRACT

A process can be used for manufacturing (S)-3-hydroxy-1-(1H-indol-5-yl)-2-oxo-pyrrolidine-3-carboxylic acid 3,5-difluoro-benzylamide.

8 Claims, No Drawings

PROCESS FOR MANUFACTURING (S)-3-HYDROXY-1-(1H-INDOL-5-YL)-2-OXO-PYRROLIDINE-3-CARBOXYLIC ACID 3,5-DIFLUORO-BENZYLAMIDE

BACKGROUND OF THE INVENTION

Field of the Invention

CROSS-REFERENCE TO RELATED APPLICATIONS

This application is the National Stage entry under § 371 of International Application No. PCT/EP2020/068317, filed on Jun. 30, 2020, and which claims the benefit of priority to European Application No. 19184056.0, filed on Jul. 3, 2019.

The invention had the object of finding novel compounds having valuable properties, in particular those which can be used for the preparation of medicaments.

The present invention relates to a process for manufacturing the MetAP-2 inhibitor (S)-3-hydroxy-1-(1H-indol-5-yl)-2-oxo-pyrrolidine-3-carboxylic acid 3,5-difluoro-benzylamide ("S-9") being synthesized in a key step with an asymmetric oxidizing agent: 'Davis oxaziridine'.

Davis oxaziridine: (+)-(2R,4aS,7S,8aR)-4H-4a, 7-Methanooxazirino[3,2-i] [2,1] benzisothiazole, 8,8-dichlorotetrahydro-9,9-dimethyl-3,3-dioxide

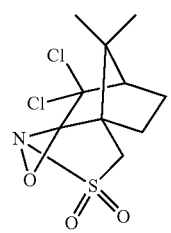 [SMILES: CC1(C)C2CCC13CS(=O)(=O)N1OC13C2(Cl)Cl]

This process for the preparation of "S-9" is not known.

Prior art references WO 2012048775, WO 2013149704 and WO 2016020031 disclose a racemic synthesis for manufacturing the racemic compound followed by chiral separation.

The analysis/comparison of both ways, the racemic synthesis vs the described asymmetric route, clearly demonstrates that the asymmetric oxidation is superior compared to the state of the art.

The asymmetric process requires less steps and is higher yielding.

Scheme 1 gives an overview of how the routes differ.

The common intermediate is compound number 5. Starting from this compound 5 the established route requires five additional synthetic steps and chiral chromatography to get the desired enantiomer S-9 in 15% overall yield.

Via 3 additional steps (R-9 to 10: alcohol activation; 10 to 11: inversion; 11 to S-9: hydrolysis) the yield can be increased but the amount of work is significantly increased.

This new process gives S-9 in three additional steps from 5 in 27% overall yield.

The key step is the enantioselective oxidation of 1-[1-(benzenesulfonyl)-1H-indol-5-yl]-N-[(3,5-difluorophenyl)methyl]-2-oxopyrrolidine-3-carboxamide (12) to give (3S)-1-[1-(benzenesulfonyl)-1H-indol-5-yl]-N-[(3,5-difluorophenyl)methyl]-3-hydroxy-2-oxopyrrolidine-3-carboxamide (13).

Scheme 1

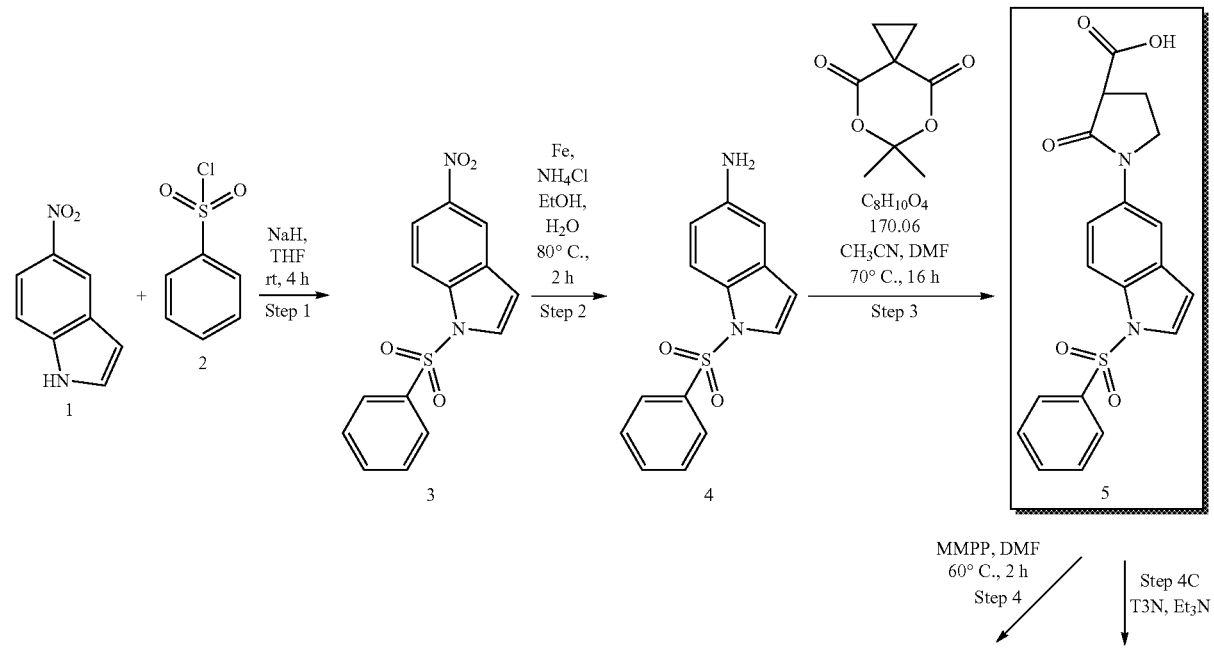

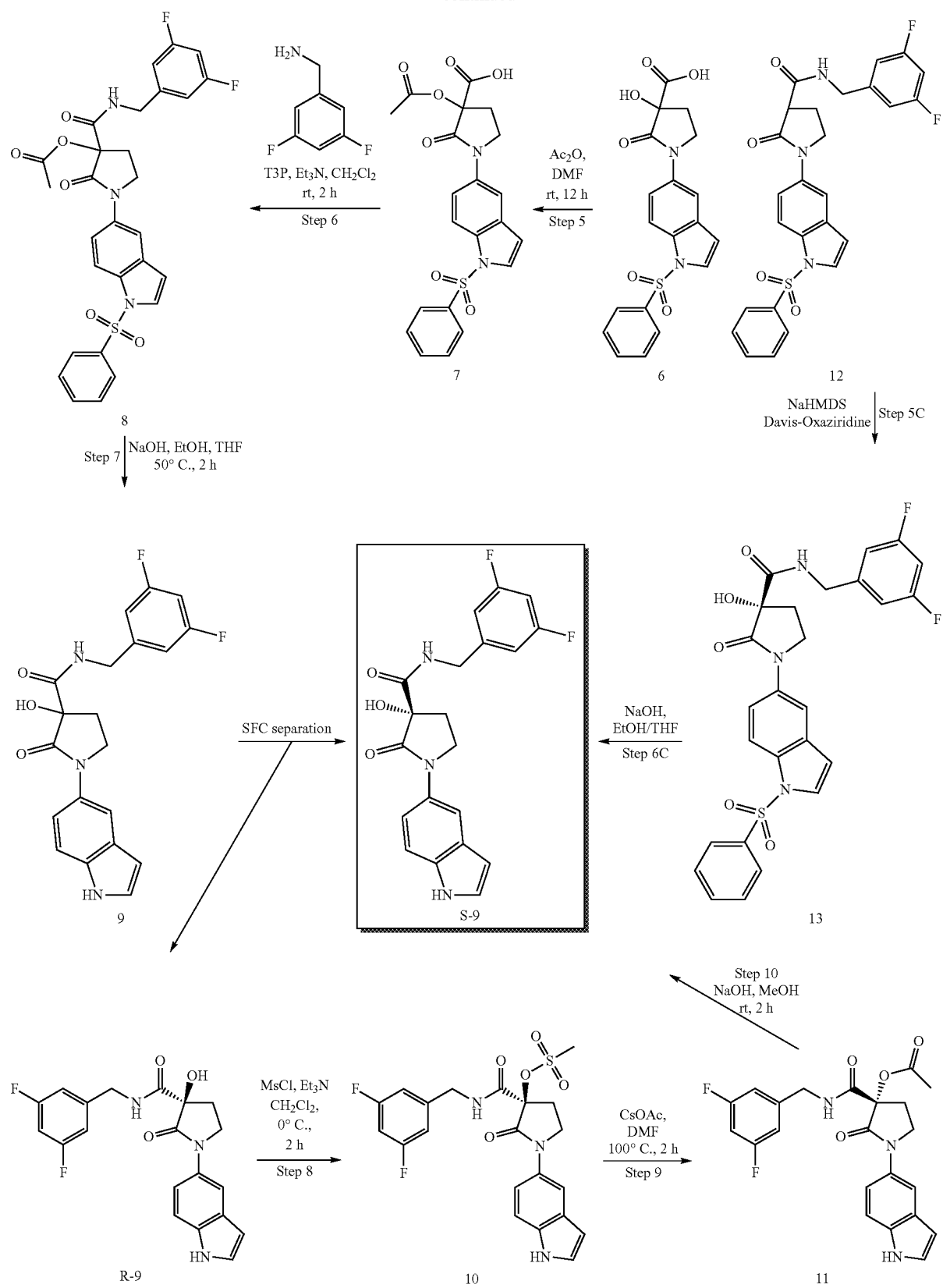

Description of Related Art

Prior art references WO 2012/048775, WO 2013/149704 and WO 2016020031 disclose a racemic synthesis for manufacturing the racemic compound followed by chiral separation.

(S)-3-hydroxy-1-(1H-indol-5-yl)-2-oxo-pyrrolidine-3-carboxylic acid 3,5-difluoro-benzylamide is disclosed as "B8" in WO 2013/149704.

SUMMARY OF THE INVENTION

The invention relates to a process for manufacturing (S)-3-hydroxy-1-(1H-indol-5-yl)-2-oxo-pyrrolidine-3-carboxylic acid 3,5-difluoro-benzylamide ("S-9"), characterized in that
a) 2-oxo-1-(1-(phenylsulfonyl)-1H-indol-5-yl)pyrrolidine-3-carboxylic acid ("5") is reacted with 3,5-difluorobenzyl amine to give 1-[1-(benzenesulfonyl)-1H-indol-5-yl]-N-[(3,5-difluorophenyl)methyl]-2-oxopyrrolidine-3-carboxamide ("12"),
b) "12" is then enantioselectively oxidized to give (3S)-1-[1-(benzenesulfonyl)-1H-indol-5-yl]-N-[(3,5-difluorophenyl)methyl]-3-hydroxy-2-oxopyrrolidine-3-carboxamide ("13"),
c) and subsequently the phenylsulfonyl group is cleaved off from "13" to give (S)-3-hydroxy-1-(1H-indol-5-yl)-2-oxo-pyrrolidine-3-carboxylic acid 3,5-difluoro-benzylamide ("S-9").

DETAILED DESCRIPTION OF THE INVENTION

Preferably the invention relates to a process for manufacturing (S)-3-hydroxy-1-(1H-indol-5-yl)-2-oxo-pyrrolidine-3-carboxylic acid 3,5-difluoro-benzylamide ("S-9"), characterized in that
2-oxo-1-(1-(phenylsulfonyl)-1H-indol-5-yl)pyrrolidine-3-carboxylic acid ("5") is reacted with 3,5-difluorobenzyl amine to give 1-[1-(benzenesulfonyl)-1H-indol-5-yl]-N-[(3,5-difluorophenyl)methyl]-2-oxopyrrolidine-3-carboxamide ("12"), "12" is then reacted with (+)-(2R,4aS,7S,8aR)-4H-4a, 7-methanooxazirino[3,2-i] [2,1] benzisothiazole, 8,8-dichlorotetrahydro-9,9-dimethyl-3,3-dioxide to give (3S)-1-[1-(benzenesulfonyl)-1H-indol-5-yl]-N-[(3,5-difluorophenyl)methyl]-3-hydroxy-2-oxopyrrolidine-3-carboxamide ("13"),
and subsequently the phenylsulfonyl group is cleaved off from "13" to give (S)-3-hydroxy-1-(1H-indol-5-yl)-2-oxo-pyrrolidine-3-carboxylic acid 3,5-difluoro-benzylamide ("S-9").

The reaction of compound 5 with 3,5-difluorobenzyl amine in step 4C is generally carried out in the presence of an organic base, such as DIPEA, triethylamine, dimethylaniline, pyridine, quinoline, diazabicycloundecene (DBU) or di-isopropylethylamine (Hünig's base). Most preferably the reaction is carried out in the presence of triethylamine, DBU or di-isopropylethylamine.

Depending on the conditions used, the reaction time is between a few minutes and 14 days, the reaction temperature is between about −30° and 140°, normally between −10° and 90°, in particular between about 0° and about 40°.

The reaction preferably is carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF, particularly preferred is dichloromethane.

The amide coupling of compound 5 with 3,5-difluorobenzyl amine preferably is carried out in the presence of $T_3P$ (propanephosphonic acid anhydride). Other preferred acid activating compounds are as follows, such as carbodiimides:
EDCI (1-ethyl-3-(3-dimethylaminopropyl)carbodiimide),
DCC (dicyclohexylcarbodiimide);
Phosphonium Salts:
BOP (benzotriazolyloxytris(dimethylamino)-phosphonium hexafluorophosphate),
PyBOP (benzotriazol-1-yl-oxytripyrrolidinophosphonium-hexafluorophosphat);
Immonium salts are described by So-Yeop Han, Young-Ah Kim: Recent development of peptide coupling reagents in organic synthesis: Tetrahedron 60, 2004, S. 2447;
Aminium Salts:
HATU: O-(7-azabenzotriazol-1-yl)-N,N,W,N'-tetramethyl-uronium-hexafluorphosphate;
HBTU (2-(1H-Benzotriazol-1-yl)-1,1,3,3-tetramethyluronium-hexafluorophosphate);
Uronium Salts:
COMU ((1-cyano-2-ethoxy-2-oxoethylidenam inooxy)dimethylamino-morpholino-carbenium-hexafluorophosphate);
Imidazolium Salts:
Imidazolium salts are described by So-Yeop Han, Young-Ah Kim: Recent development of peptide coupling reagents in organic synthesis: Tetrahedron 60, 2004, S. 2447;
HObt (Hydroxybenzotriazole).

The oxidation of compound 12 to compound 13 in step C5 preferably is carried out in an organic solvent such as THF or diethylether.

The reaction generally is carried out in the presence of a base, such as NaHMDS (sodium-hexamethyldisilazane), LiHMDS (lithium-hexamethyldisilazane), KHMDS (potassium-hexamethyldisilazane), LDA (lithium diisopropylamide), BuLi (buthyl lithium) or potassium tert-butylate. Particular preference is given to NaHMDS.

The reaction is preferably carried out with the asymmetric oxidation reagent (+)-(2R,4aS,7S,8aR)-4H-4a, 7-Methanooxazirino[3,2-i] [2,1] benzisothiazole, 8,8-dichlorotetrahydro-9,9-dimethyl-3,3-dioxide

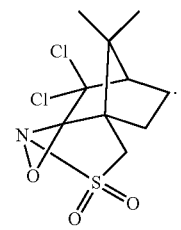 [SMILES: CC1(C)C2CCC13CS(=O)(=O)N1OC13C2(Cl)Cl]

Instead of the dichloro compound the dibromo or difluoro compounds are preferred.

The reaction of compound 13 to compound S-9 (cleavage of the phenylsulfonyl group) in step C6 most preferably is carried out with an alkali or alkaline earth metal hydroxide, carbonate or bicarbonate or another salt of a weak acid of the alkali or alkaline earth metals, preferably of potassium, sodium, calcium or caesium, may also be favourable.

The reaction preferably is carried out in an inert solvent.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol and/or THF.

The reaction of compound 13 to compound S-9 (cleavage of the phenylsulfonyl group) in step C6 most preferably is carried out with NaOH in a mixture of ethanol/THF.

More preferably, the cleavage of the phenyl sulfonyl group from the indole ring is carried out as follows:
with tetrabutyl ammonium fluoride in THF;
with magnesium or lithium tert-butoxide in THF;
with sodium tert-butylate in dioxane;
with 1-(N,N-dimethylamino)pyrene, triethylamine in acetonitrile;
with titanium(IV)isopropylate, chloro-trimethyl-silane, magnesium in THF.

EXAMPLES

Step-1: 3

[5-nitro-1-(phenylsulfonyl)-1H-indole]

Reaction scheme

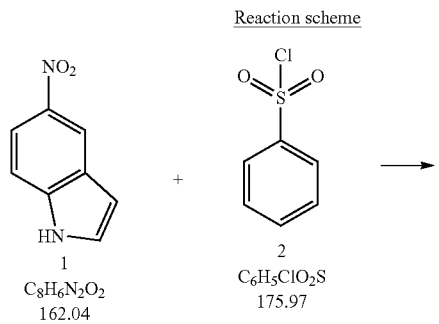

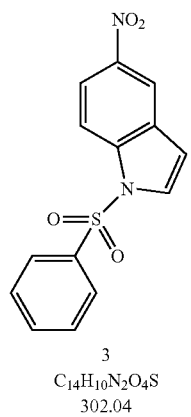

3
$C_{14}H_{10}N_2O_4S$
302.04

Experimental Procedure 5-nitro indole 1 (500 g, 3.08 mol) was dissolved in THF (5 L) and the mixture was cooled to 0° C. and stirred for 20 minutes. Sodium hydride (140 g, 3.5 mol) was added in portions and the mixture was stirred for additional 30 minutes at 15° C. Benzene sulphonyl chloride 2 (475 mL, 3.7 mol) was introduced through an additional funnel for 30 minutes under stirring. After completion of the addition the mixture was stirred for 4 hours. After completion of the reaction, the reaction mass was cooled to 0° C. and quenched with ice (3 L). Ethyl acetate (5 L) and water (2.5 L) were added. After phase separation the aqueous layer was re-extracted with ethyl acetate (5 L). The combined organic layer was dried over sodium sulphate and concentrated under reduced pressure at 55° C. Ethyl acetate/pet. ether (8%, 5 L) were added to the crude mass and the mixture was stirred for 20 min at room temperature. The product was filtered and washed with ethyl acetate and pet. ether mixture (5%, 2 L). The product was dried under vacuum to give 3 as a yellow solid.

Yield 890 g (95%).

$^1$H NMR (400 MHz, DMSO-$d_6$) δ 8.63-8.55 (m, 1H), 8.26-8.14 (m, 2H), 8.13-8.02 (m, 3H), 7.79-7.70 (m, 1H), 7.69-7.59 (m, 2H), 7.10 (d, J=3.7 Hz, 1H); Molecular Formula: $C_{14}H_{10}N_2O_4S$; HPLC purity: 99.92%; Expected LCMS Mass: 302.0; Observed: 161.2 (M-141).

Step-2: 4

1-(phenylsulfonyl)-1H-indol-5-amine

Step-3: 5

2-oxo-1-(1-(phenylsulfonyl)-1H-indol-5-yl)pyrrolidine-3-carboxylic acid

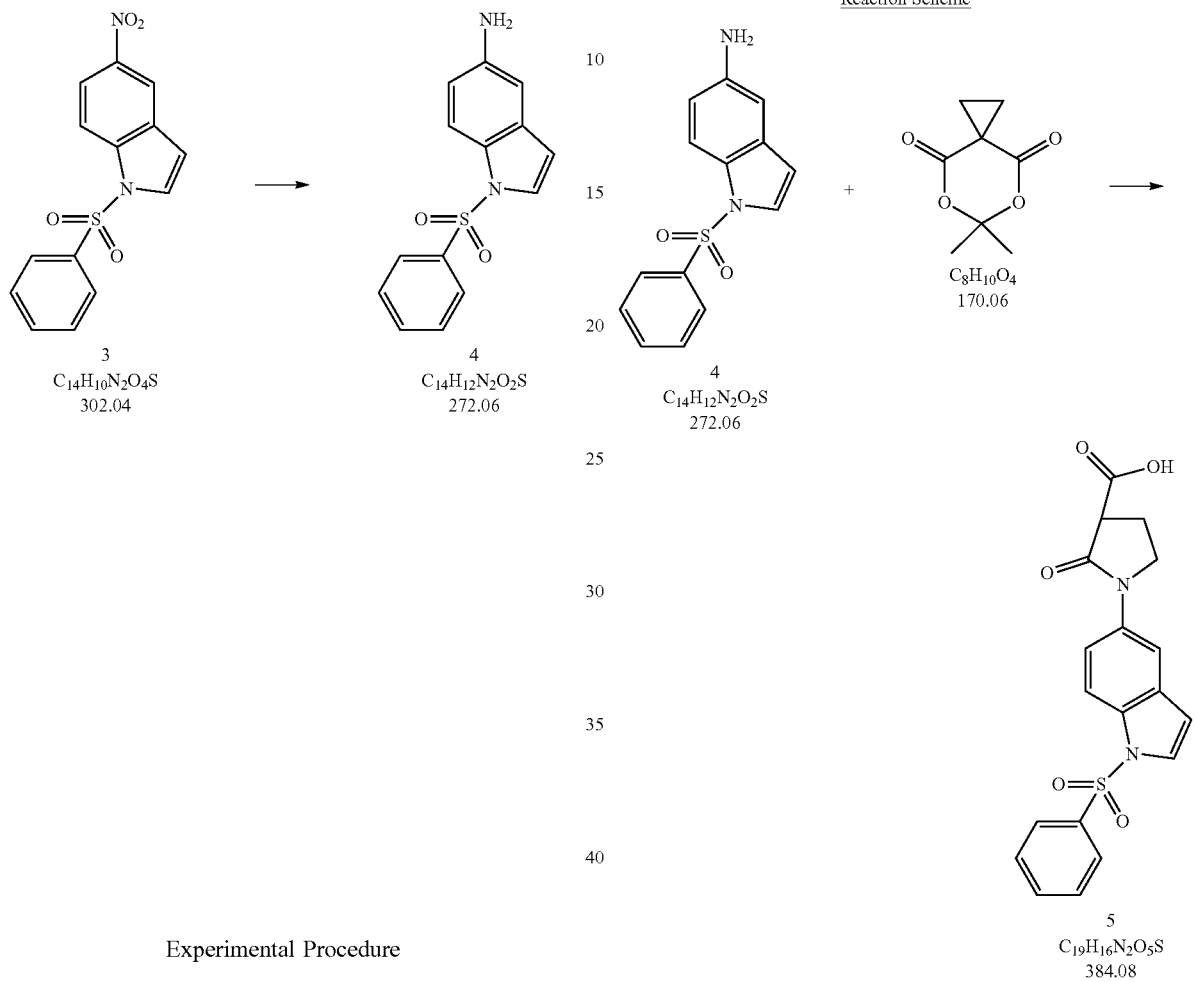

Experimental Procedure

Step-1 product 3 (500 g, 1.65 mol) was dissolved in ethanol (7 L). Iron powder was added (500 g, 8.95 mol) and the mixture was heated to 50° C. After 15 minutes, a solution of NH$_4$Cl (1 kg, 18.69 mol) in water (3.1 L) was added to the reaction mixture through an additional funnel for 1 hour. The reaction mixture was heated to 80° C. for 2 hours. After completion of the reaction, the reaction mass was cooled to 40° C., filtered through celite and concentrated under reduced pressure at 50° C. Ethyl acetate and water (5 L each) were added and the layers were separated. The aq. layer was re-extracted with ethyl acetate (5 L). The combined organic layer was dried over sodium sulphate and concentrated under reduced pressure at 50° C. The remainder was suspended in ethyl acetate/pet. ether (5%, 5 L) and then cooled to room temperature. The product was filtered and washed with ethyl acetate/pet. ether (5%, 5 L). The product was dried under vacuum to give 4 as a brown solid.

Yield 400 g (89%).

$^1$H NMR (300 MHz, DMSO-d$_6$) δ 7.86 (d, J=7.5 Hz, 2H), 7.70-7.42 (m, 5H), 6.67-6.48 (m, 3H), 4.97 (s, 2H); Molecular Formula: C$_{14}$H$_{12}$N$_2$O$_2$S; HPLC purity: 97.25%; Expected LCMS Mass: 272.1; Observed: 273.0 (M+1).

Experimental Procedure

Step-2 product 4 (1.6 kg, 5.87 mol) and cyclopropyl meldrum acid (1.2 kg, 7.05 mol) were given into the reactor followed by acetonitrile (5.5 L) and DMF (1.9 L). The mixture was heated to 70° C. for 16 hours under nitrogen atmosphere. After completion of the reaction, the reaction mass was concentrated under reduced pressure at 50-55° C. The residue was cooled and treated with water and ethyl acetate (10 L each). After phase separation the organic layer was washed with brine (5 L), dried over sodium sulphate and concentrated under reduced pressure at 40-45° C. The obtained crude solid was washed with ethyl acetate/pet. ether (5%, 2 L) giving 5 as brown solid.

Yield: 1.8 kg (80%).

$^1$H NMR (300 MHz, DMSO-d$_6$) δ 12.80 (br.s., 1H), 8.02-7.85 (m, 3H), 7.85-7.74 (m, 2H), 7.71-7.47 (m, 4H), 6.84 (d, J=3.6 Hz, 1H), 3.94-3.76 (m, 2H), 3.57 (t, J=8.5 Hz, 1H), 2.37-2.20 (m, 2H); Molecular Formula: C$_{19}$H$_{16}$N$_2$O$_5$S; HPLC purity: 91.51%; Expected LCMS Mass: 384.08; Observed: 385.0 (M+1).

5 is the starting point for both procedures, the racemic and the asymmetric syntheses.

Step-4: 6

3-hydroxy-2-oxo-1-(1-(phenylsulfonyl)-1H-indol-5-yl)pyrrolidine-3-carboxylic acid

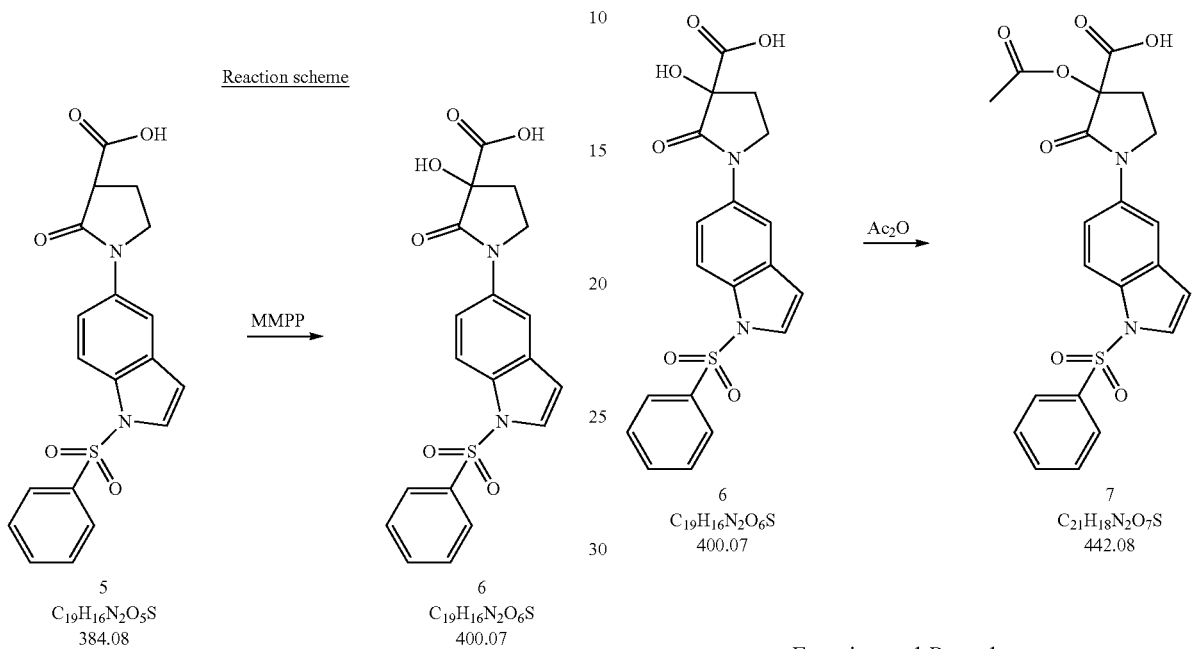

Experimental Procedure

Step-3 product 5 (1.0 kg, 2.60 mol) was treated with DMF (8.5 L) and Magnesium monoperoxyphthalate hexahydrate 80% (1.9 kg, 3.84 mol). The mixture was heated to 60° C. for 2 hours under nitrogen atmosphere. After completion of the reaction, the reaction mass was concentrated under reduced pressure at 50-55° C. The residue was taken in water (5 L) and ethyl acetate (3 L) and stirred for 12 hours at room temperature. The product was filtered and washed with water and ethyl acetate (3 L each). The product was dried under vacuum at 65° C. to give 6 as off white solid.

Yield: 700 g (67%).

Note: Moisture content of the step 4 product should be less than 0.5%.

$^1$H NMR (400 MHz, DMSO-$d_6$) δ 7.97-7.94 (m, 3H), 7.87 (s, 1H), 7.81 -7.80 (d, J=3.4 Hz, 1H), 7.73-7.66 (m, 2H), 7.60-7.56 (m, 2H), 7.16 (br.s, 1H), 6.87 (d, J=3.4 Hz, 1H), 3.92 (q, J=8.4 Hz, 1H), 3.75 (t, J=8.7 Hz, 1H), 3.45-3.42 (m, 1H), 2.43-2.38 (m, 1H), 2.03-1.96 (m, 1H); Molecular Formula: $C_{19}H_{16}N_2O_6S$; HPLC purity: 96.12%; Expected LCMS Mass: 400.07; Observed: 401.0 (M+1).

Step-5: 7

3-acetoxy-2-oxo-1-(1-(phenylsulfonyl)-1H-indol-5-yl) pyrrolidine-3-carboxylic acid

Experimental Procedure

Step-4 product 6 (1.0 kg, 2.5 mol) and DMF (8 L) were given into a reactor at room temperature and stirred for 10 minutes. Acetic anhydride (355 mL, 3.75 mol) was added slowly to the mass and the mixture was stirred for 12 hours. After completion of the reaction, the reaction mass was concentrated under reduced pressure at 50-55° C. The residue was cooled to 0° C., suspended with water (5 L) and stirred for overnight at room temperature. The precipitate was filtered, washed with water (3 L) and then suspended in acetone (3 L) for 1 hour. Filtration gave product 7 as white solid, which was dried under vacuum at 65° C.

Yield: 940 g (85%).

Note: Moisture content of the step 5 product should be less than 0.5%.

$^1$H NMR (400 MHz, DMSO-$d_6$) δ 7.98-7.89 (m, 3H), 7.86-7.77 (m, 2H), 7.73-7.62 (m, 2H), 7.60-7.51 (m, 2H), 6.85 (d, J=3.8 Hz, 1H), 3.98 (q, J=8.1 Hz, 1H), 3.72 (t, J=9.0 Hz, 1H), 2.79 (dd, J=7.3, 12.1 Hz, 1H), 2.22-2.09 (m, 1H), 2.01 (s, 3H); Molecular Formula: $C_{21}H_{18}N_2O_7S$; HPLC purity: 97.83%; Expected LCMS Mass: 442.08; Observed: 443.0 (M+1).

NB

Reaction mixture should be concentrated below 55° C. and evaporation should be complete within 2 hours. Higher temperature and prolong heating leads to de-carboxylation of the product.

Step-6: 8

3-((3,5-difluorobenzyl)carbamoyl)-2-oxo-1-(1-(phenylsulfonyl)-1H-indol-5-yl)pyrrolidin-3-yl acetate.

Reaction scheme

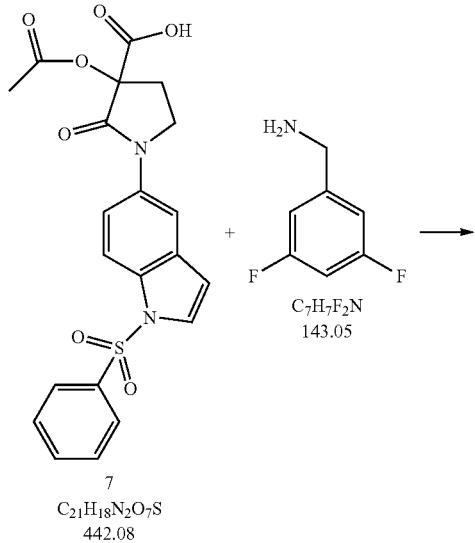

7
C$_{21}$H$_{18}$N$_2$O$_7$S
442.08

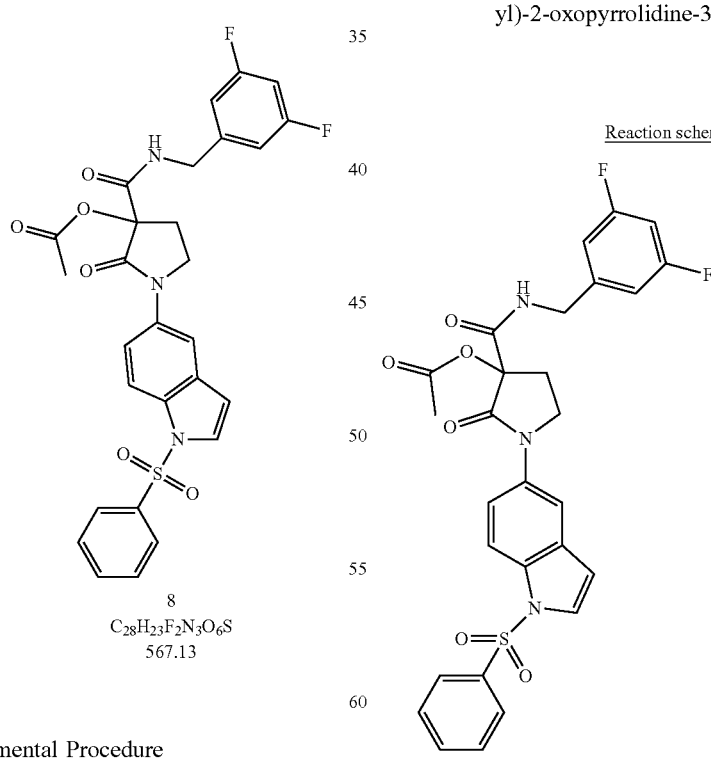

8
C$_{28}$H$_{23}$F$_2$N$_3$O$_6$S
567.13

Experimental Procedure

Step-5 product 7 (1.0 kg, 2.26 mol) was dissolved in CH$_2$Cl$_2$ (10 L) at room temperature for 10 minutes and then cooled to 0° C. Triethyl amine (690 mL, 4.95 mol), 3,5-difluorobenzyl amine (405 g, 2.83 mol) and 2,4,6-tripropyl-[1,3,5,2,4,6]trioxatriphosphinane 2,4,6-trioxide (2.15 L, 3.38 mol) were added and the reaction mixture was stirred at room temperature for 2 hours. After completion of the reaction, the reaction mass was diluted with water (5 L) and stirred for 10 minutes. The aqueous layer was removed from the top. This aqueous washing was repeated 3 times. The organic layer was filtered and the precipitate was washed with CH$_2$Cl$_2$ (1 L) and acetone (0.5 L) to get 8 as off white solid.

Yield: 1.07 kg (83%).

$^1$H NMR (400 MHz, DMSO-d$_6$) δ 8.99 (t, J=6.2 Hz, 1H), 7.97 (d, J=8.1 Hz, 3H), 7.83 (dd, J=2.8, 5.2 Hz, 2H), 7.72-7.63 (m, 2H), 7.62-7.53 (m, 2H), 7.06 (t, J=9.4 Hz, 1H), 6.93 (d, J=7.0 Hz, 2H), 6.87 (d, J=3.5 Hz, 1H), 4.33 (dq, J=6.0, 16.1 Hz, 2H), 3.99-3.83 (m, 2H), 2.88 (ddd, J=2.6, 7.9, 13.2 Hz, 1H), 2.43-2.28 (m, 1H), 2.18 (s, 3H); Molecular Formula: C$_{28}$H$_{23}$F$_2$N$_3$O$_6$S; HPLC purity: 99.88%; Expected LCMS Mass: 567.13; Observed: 568.0 (M+1).

Step-7: 9

N-(3,5-difluorobenzyl)-3-hydroxy-1-(1H-indol-5-yl)-2-oxopyrrolidine-3-carboxamide Reaction scheme

9
C₂₀H₁₇F₂N₃O₃
385.12

Experimental Procedure

Step-6 product 8 (1.2 kg, 2.11 mol) was dissolved in ethanol (5 L) and THF (10 L) and stirred at room temperature for 10 minutes. Sodium hydroxide (422 g, 10.55 mol) was added and stirred for 2 hours at 50° C. After completion of the reaction, the reaction mass was concentrated under reduced pressure at 45° C. The residue was dissolved in ethyl acetate (10 L) and water (5 L). After phase separation the organic layer was washed with water (2×5 L) and brine (5 L). The organic layer was dried over sodium sulphate, filtered and concentrated under reduced pressure at 45-50° C. $CH_2Cl_2$ (1 L) was added to the remainder and the precipitate was filtered and washed with $CH_2Cl_2$ (1.0 L) to give 9 as off white solid.

Yield: 700 g (86%).

$^1$H NMR (400 MHz, DMSO-d$_6$) δ 11.12 (br.s., 1H), 8.69 (t, J=6.4 Hz, 1H), 7.70 (s, 1H), 7.46-7.32 (m, 3H), 7.12-6.94 (m, 3H), 6.69 (s, 1H), 6.47-6.38 (m, 1H), 4.41 (dd, J=6.9, 16.0 Hz, 1H), 4.25 (dd, J=5.9, 15.8 Hz, 1H), 3.94-3.81 (m, 2H), 2.66-2.54 (m, 1H), 2.13 (td, J=7.6, 13.0 Hz, 1H); Molecular Formula: $C_{20}H_{17}F_2N_3O_3$; HPLC purity: 98.11%; Expected LCMS Mass: 385.12; Observed: 386.0 (M+1).

SFC Separation:
Isomers of 9 (5.20 Kg) were separated via SFC purification.
SFC Method:
Column: Lux Amylose-2 (250×30) mm, 5 micron
Mobile phase: $CO_2$: MeOH (60:40)
Flow rate: 200 g/min
Run time: 10 min (cycle time)
Loading per injection: 700 mg

| Quantity input 9 | Quantity Output | | |
|---|---|---|---|
| | S-9 (Fraction 1) | Mixture of fraction 1 & 2 | R-9 (Fraction 2) |
| 5.20 Kg | 1.93 Kg (37%) | 0.60 Kg | 1.80 Kg |

Fraction 1 (S-9): $^1$H NMR (400 MHz, DMSO-d$_6$) δ 11.12 (br.s., 1H), 8.69 (t, J=6.4 Hz, 1H), 7.70 (s, 1H), 7.46-7.32 (m, 3H), 7.12-6.94 (m, 3H), 6.69 (s, 1H), 6.47-6.38 (m, 1H), 4.41 (dd, J=6.9, 16.0 Hz, 1H), 4.25 (dd, J=5.9, 15.8 Hz, 1H), 3.94-3.81 (m, 2H), 2.66-2.54 (m, 1H), 2.13 (td, J=7.6, 13.0 Hz, 1H); Molecular Formula: $C_{20}H_{17}F_2N_3O_3$; HPLC purity: 99.46%; Chiral HPLC purity: 100%; Expected LCMS Mass: 385.12; Observed: 386.0 (M+1); SOR: +14.69.

Fraction 2 (R-9): $^1$H NMR (400 MHz, DMSO-d$_6$) δ 11.12 (br.s., 1H), 8.69 (t, J=6.3 Hz, 1H), 7.73-7.68 (m, 1H), 7.45-7.31 (m, 3H), 7.11-6.94 (m, 3H), 6.69 (s, 1H), 6.46-6.38 (m, 1H), 4.41 (dd, J=6.7, 15.8 Hz, 1H), 4.25 (dd, J=5.9, 15.8 Hz, 1H), 3.94-3.79 (m, 2H), 2.66-2.56 (m, 1H), 2.13 (td, J=7.6, 13.0 Hz, 1H); Molecular Formula: $C_{20}H_{17}F_2N_3O_3$; HPLC purity: 97.20%; Chiral HPLC purity: 98.17%; Expected LCMS Mass: 385.12; Observed: 386.2 (M+1); SOR: −13.49.

Mixture of fraction (1 & 2): HPLC purity: 98.90%; Chiral HPLC purity: 32.99% (fraction 1) & 67.01 (fraction 2).

Yield optimization can be achieved by inversion of the chiral centre. The invented procedure is outlined.

Step 8: 10

(R)-3-((3,5-difluorobenzyl)carbamoyl)-1-(1H-indol-5-yl)-2-oxopyrrolidin-3-yl methanesulfonate Reaction scheme

Experimental Procedure

To an ice cooled solution of R-9 (200 g, 0.52 mol) in dry $CH_2Cl_2$ (2 L), was added $Et_3N$ (252 ml, 1.81 mol) followed by drop wise addition of Mesyl chloride (80.4 ml, 1.03 mol). The reaction mixture was stirred at the same temperature for another 2 hours. After completion, reaction mixture was washed with water (1.5 L), 5% Citric acid (1 L) and saturated aqueous solution of $NaHCO_3$ (1×5 L). The combined organic extracts were washed with brine (1 L), dried over Na$_2$SO$_4$, filtered and concentrated under vacuum yielded 10 (260 g). The crude product was directly taken for next step without further purification.

Molecular Formula: C$_{21}$H$_{19}$F$_2$N$_3$O$_5$S; HPLC purity: 81.76%; Expected LCMS Mass: 463.10; Observed: 464.0 (M+1).

Step 9: 11

(S)-3-((3,5-difluorobenzyl)carbamoyl)-1-(1H-indol-5-yl)-2-oxopyrrolidin-3-yl acetate Reaction Scheme

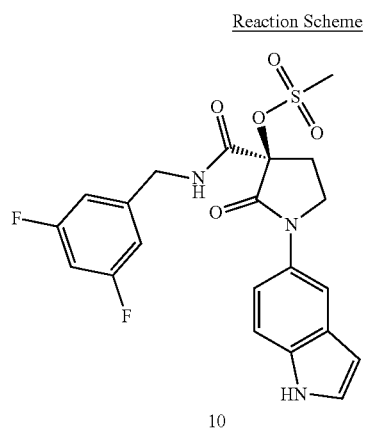

10

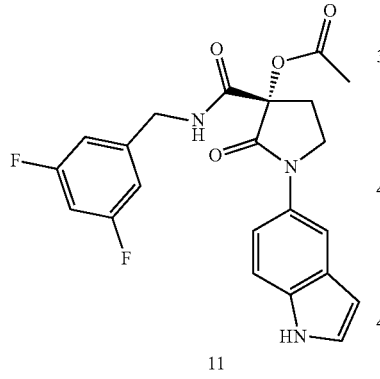

11

Experimental Procedure

To a solution of cesium acetate (214 g, 1.12 mol) in dry DMF (1.2 L) at 100° C. was added a solution of 10 (260 g, 0.560 mol) in DMF (1.0 L) dropwise over 20 minutes through an addition funnel. The heating was continued for another 1.5 hours. After completion, the reaction mass was concentrated under vacuum. The crude mass was dissolved in ethyl acetate (2 L) and washed with water (2×2 L). The combined organic extracts were washed with brine (1 L), dried over Na$_2$SO$_4$, filtered and concentrated under vacuum to yield 11 (250 g). The crude product was directly taken for next step without further purification.

Molecular Formula: C$_{22}$H$_{19}$F$_2$N$_3$O$_4$; HPLC purity: 45.64%; Expected LCMS Mass: 427.13; Observed: 428.3 (M+1).

Step 10: S-9

(S)-N-(3,5-difluorobenzyl)-3-hydroxy-1-(1H-indol-5-yl)-2-oxopyrrolidine-3-carboxamide Reaction Scheme

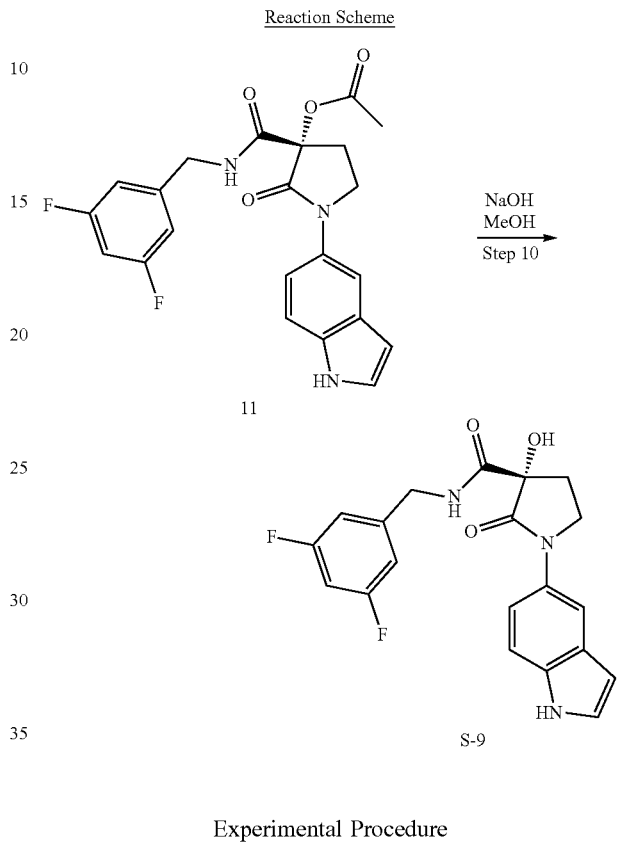

Experimental Procedure

To an ice cooled solution of the crude 11 (250 g 0.52 mol) in methanol (2.5 L) was added NaOH pellets (63 g, 1.56 mol). The reaction mixture was stirred at RT for 2 hours. After completion, methanol was concentrated under vacuum at <55° C. The crude mass was dissolved in ethyl acetate (2 L) and washed with water (3×2 L). The combined organic extracts were washed with brine (1 L), dried over Na$_2$SO$_4$, filtered and concentrated under vacuum. It was passed through a wash column (Silica 60-120) and nonpolar impurities were removed using 30-40% ethyl acetate/pet. ether. The product was eluted with 3-5% MeOH/CH$_2$Cl$_2$. The isolated product was dissolved in minimum amount of ethyl acetate and kept in cold room for 16 hours. The solid formed was filtered through a Büchner funnel, washed with ethyl acetate (3×100 ml) to give S-9 (56 g, 28% in three steps) as off white solid.

Dried solid was milled in a pin mill (6000 rpm, 30 min) to obtain final API.

$^1$H NMR (400 MHz, DMSO-d$_6$) δ 11.12 (br.s., 1H), 8.69 (t, J=6.4 Hz, 1H), 7.70 (s, 1H), 7.46-7.32 (m, 3H), 7.12-6.94 (m, 3H), 6.69 (s, 1H), 6.47-6.38 (m, 1H), 4.41 (dd, J=6.9, 16.0 Hz, 1H), 4.25 (dd, J=5.9, 15.8 Hz, 1H), 3.94-3.81 (m, 2H), 2.66-2.54 (m, 1H), 2.13 (td, J=7.6, 13.0 Hz, 1H); Molecular Formula: C$_{20}$H$_{17}$F$_2$N$_3$O$_3$; HPLC purity: 98.72%; Chiral HPLC purity: 98.68%; (ee: 97.36%); Expected LCMS Mass: 385.12; Observed: 386.2 (M+1).

Particle size: <18 μm.
SOR: +13.62.
MP: 195.3-198.9° C.
MC: 0.21%
RESIDUAL SOLVENTS:

Methanol --- 17 ppm
Ethanol --- ND
ACN --- ND
$CH_2Cl_2$ --- ND
Ethyl acetate --- 75 ppm
THF --- 206 ppm
n-Heptane --- 47 ppm Step-4C: 12

1-[1-(benzenesulfonyl)-1H-indol-5-yl]-N-[(3,5-difluorophenyl)methyl]-2-oxopyrrolidine-3-carboxamide

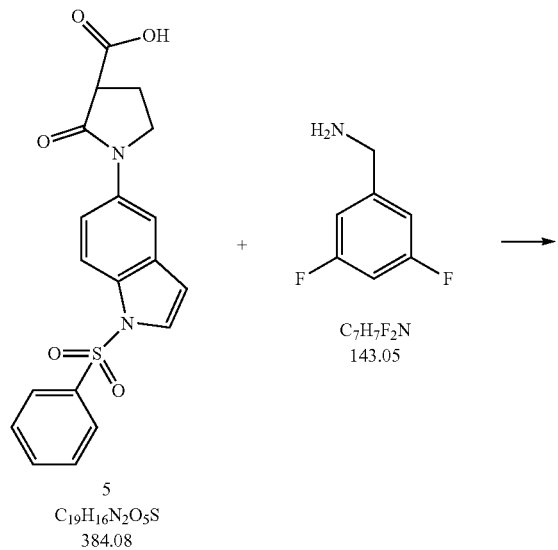

Experimental Procedure

To an ice cooled solution of 5 (750 g, 1.95 mol) in $CH_2Cl_2$ (7 L), $Et_3N$ (600 mL, 4.29 mol) was added followed by 3,5-difluorobenzyl amine (363 g, 2.53 mol). $T_3P$ (Propane-phosphonic acid anhydride) (1.86 L (50% EA [ethyl acetate] solution), 3.0 mol) was added dropwise into the reaction mixture slowly and the reaction mixture was stirred at RT for 2 h. After completion of the reaction, the reaction mass was quenched with water (3 L) and stirred for 10 minutes. The organic layer was separated and washed with 10% $NaHCO_3$ solution (2 L) followed by water wash (3 L×3). The organic phase was finally washed with brine (3 L), dried over anhydrous sodium sulfate and concentrated to get the crude product as light brown solid. It was made slurry with minimum amount of ethyl acetate (1.5 L) and filtered. The cake was washed with ice cold ethyl acetate (1 L×2) to get the pure product as off white solid with HPLC >99%. Amount obtained: 720 g; Yield: 72%;

$^1$H-NMR (400 MHz, DMSO-$d_6$): δ 8.82 (t, J=5.60 Hz, 1H), 7.99-7.94 (m, 3H), 7.83 (d, J=2.80 Hz, 2H), 7.71-7.67 (m, 2H), 7.61-7.57 (m, 2H), 7.12-7.05 (m, 3H), 6.87 (d, J=3.60 Hz, 1H), 4.49 (dd, J=6.80, 16.20 Hz, 1H), 4.27 (dd, J=5.20, 16.00 Hz, 1H), 3.90-3.85 (m, 2H), 3.63 (t, J=8.80 Hz, 1H), 2.40-2.27 (m, 2H).

Step C5: 13

(3S)-1-[1-(benzenesulfonyl)-1H-indol-5-yl]-N-[(3,5-difluorophenyl)methyl]-3-hydroxy-2-oxopyrrolidine-3-carboxamide

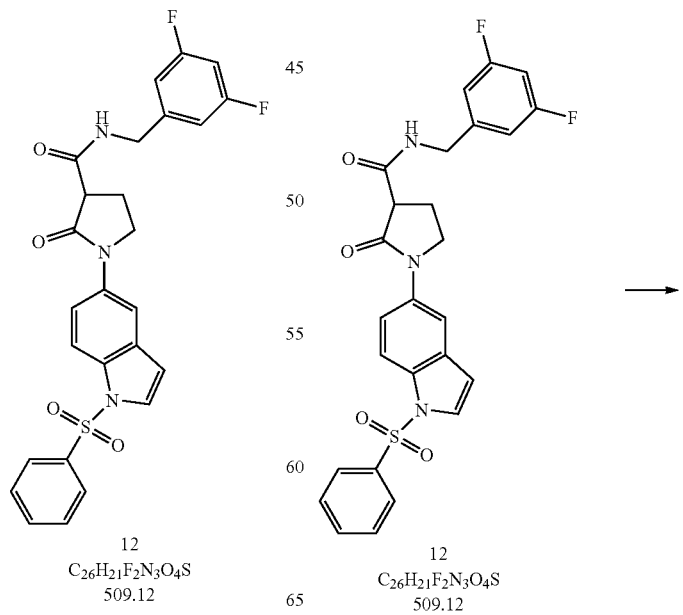

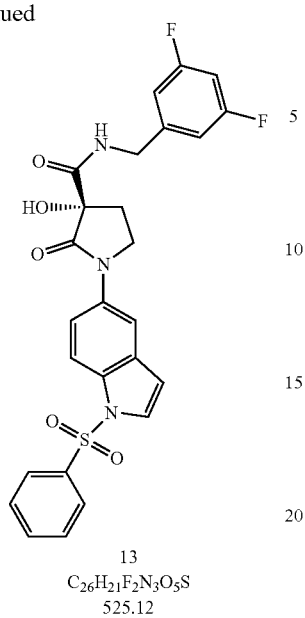

13
C26H21F2N3O5S
525.12

Experimental Procedure

A suspension of 12 (500 g, 0.98 mol) in dry THF (7.5 L) was cooled to −68° C. (inside temperature). NaHMDS solution (1078 mL, 1M in THF, 1.078 mol) was added drop wise over a period of 1.5 h while maintaining the same temperature range. After the complete addition, the reaction mixture temperature was allowed to rise to −55° C. in another 1 h and then recooled to −68° C. inside. To the yellow reaction mixture was added a solution of ((+)-(2R, 4aS, 7S, 8aR)-4H-4a, 7-methanooxazirino[3,2-i] [2,1] benzisothiazole, 8,8-dichlorotetrahydro-9,9-dimethyl-3,3-dioxide (365 g, 1.22 mol) in THF (1.1 L) dropwise over a period of 1.3 h at the same temperature. The reaction mass was allowed to come to −25° C. in another 1.5 h. After the complete conversion the system was quenched at −15° C. with ice/water (2 L). Ethyl acetate (5 L) was added to the reaction mixture, the organic layer was separated and washed with water (3 L). The aqueous layer was saturated with NaCl and re-extracted with ethyl acetate (1 L). The combined organic layer was finally washed with brine, dried over Na$_2$SO$_4$ and concentrated to get the crude product which was purified by column chromatography (SiO$_2$ 230-400 mesh). The product eluted in 50-60% ethyl acetate and was obtained as off-white solid.

Amount obtained: 375 g; Yield: 73%.

$^1$H NMR (500 MHz, DMSO-d$_6$) ppm=8.67 (t, J=6.4, 1H), 7.98-7.92 (m, 3H), 7.86 (d, J=2.2, 1H), 7.82 (d, J=3.7, 1H), 7.75-7.65 (m, 2H), 7.61-7.55 (m, 2H), 7.05 (tt, J=9.3, 2.4, 1H), 7.01-6.93 (m, 2H), 6.89 - 6.84 (m, 1H), 6.72 (s, 1H), 4.39 (dd, J=15.8, 6.8, 1H), 4.25 (dd, J=15.8, 6.0, 1H), 3.90-3.83 (m, 2H), 2.65-2.54 (m, 1H), 2.17-2.09 (m, 1H). LCMS system A: H2O+0.05% HCOOH|system B: MeCN+ 0.04% HCOOH; T: 30° C.|Flow:2.4 ml/min|Column: Chromolith RP-18e 100-3|MS:85-800 amu. Gradient: 4%-->100% (B) 0-->2.8 min|100% (B) 2.8-3.3 min. retention time: 2.376 min (M+H$^+$): 526.1.

Note: Average chiral purity achieved in this step was 85% and the maximum was 87%. It is important that any washing of crude will result in a considerable reduction in the chiral purity.

Structure of Davis Oxaziridine

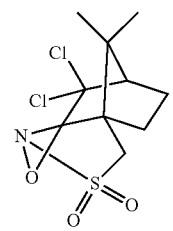 [SMILES: CC1(C)C2CCC13CS(=O)(=O)N1OC13C2(Cl)Cl]

Step C6: S-9

(S)-3-Hydroxy-1-(1H-indol-5-yl)-2-oxo-pyrrolidine-3-carboxylic acid 3,5-difluoro-benzylamide

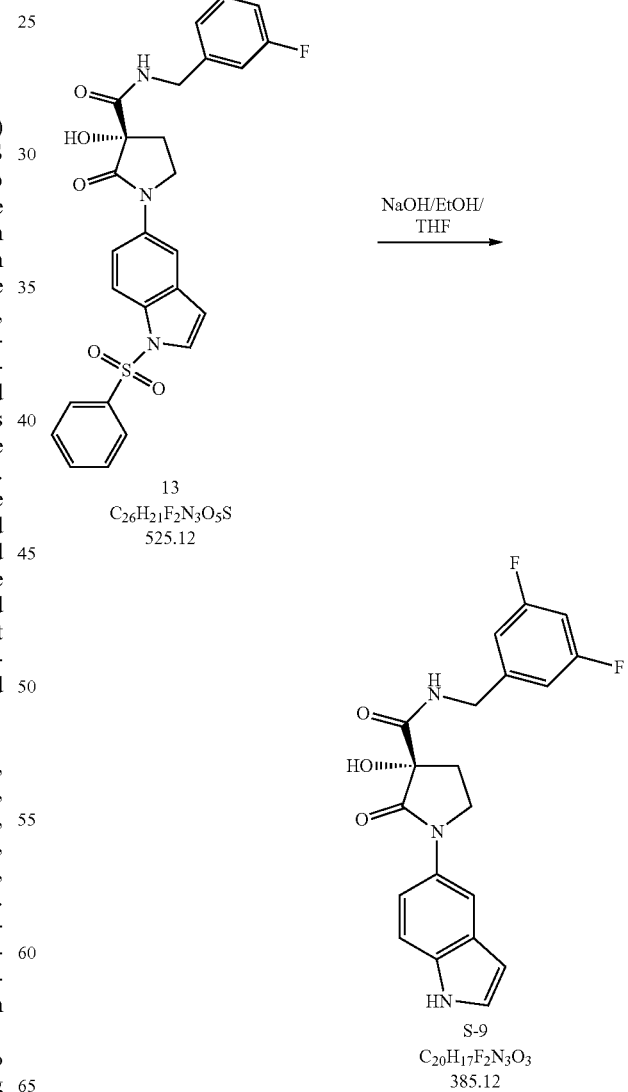

Experimental Procedure

Sodium hydroxide pellets (140 g, 3.56 mol) were added to a stirred suspension of 13 (375 g, 0.71 mol) in ethanol/THF mixture (3 L/1 L) at RT. The reaction mixture was heated at 50° C. for 2 h. After the complete conversion the reaction mixture was concentrated to get the crude mass. Water (4 L) was added and stirred for 1 h at RT. The solid formed was filtered through a Buchner funnel, neutralized by washing with 1.5 N HCl followed by water (1 L×3). The residue was finally washed with ether (2 L) to get the crude product. The chiral purity of the compound was checked at this stage and found to be 95.5%. To increase the chiral purity the solid was dissolved in minimum amount of THF/ethyl acetate (9:1) and heated to reflux at 60° C. for 30 min. The solution was filtered through a Büchner funnel and the clear filtrate was ice cooled for 2-3 h and the solid formed was filtered. The filtrate was ice cooled again for 2 h and the solid was separately filtered. Chiral purity of each solid was checked and all the fractions were mixed with ee >98.7% and finally purified by column chromatography (SiO$_2$ 230-400 mesh) using DCM/MeOH as the eluent. The pure product was eluted with 2% methanol, concentrated under reduced pressure to get the desired S-9 as off white solid. The product was dried at 60° C. for 12 h Amount obtained: 140 g; Yield: 51%.

Note 01: If the chiral purity of the crude S-9 was >97%, the mass was treated with minimum volume of ethyl acetate/THF (3V, 9:1), stirred for 30 min at RT and filtered to give desired chiral purity >98.7%

Note 02: The main aqueous layer collected was acidified with 2N HCl and the solid formed was filtered. The cake was neutralized by washing with water and finally washed with cold ethyl acetate to give remaining compound with chiral purity of 60%.

The invention claimed is:

1. A process for manufacturing (S)-3-hydroxy-1-(1H-indol-5-yl)-2-oxo-pyrrolidine-3-carboxylic acid 3,5-difluoro-benzylamide, the process comprising:

a) reacting 2-oxo-1-(1-(phenylsulfonyl)-H-indol-5-yl)pyrrolidine-3-carboxylic acid with 3,5-difluorobenzyl amine, to give 1-[1-(benzenesulfonyl)-1H-indol-5-yl]-N-[(3,5-difluorophenyl)methyl]-2-oxopyrrolidine-3-carboxamide,
   b) enantioselectively oxidizing the 1-[1-(benzenesulfonyl)-1H-indol-5-yl]-N-[(3,5-difluorophenyl)methyl]-2-oxopyrrolidine-3-carboxamide, to give (3S)-1-[1-(benzenesulfonyl)-1H-indol-5-yl]-N-[(3,5-difluorophenyl)methyl]-3-hydroxy-2-oxopyrrolidine-3-carboxamide, and
   c) subsequently cleaving off a phenylsulfonyl group from the (3S)-1-[1-(benzenesulfonyl)-1H-indol-5-yl]-N-[3,5-difluorophenyl)methyl]-3-hydroxy-2-oxopyrrolidine-3-carboxamide, to give (S)-3-hydroxy-1-(1H-indol-5-yl)-2-oxo-pyrrolidine-3-carboxylic acid 3,5-difluoro-benzylamide.

2. The process according to claim 1, wherein a) is carried out presence of a base selected from the group consisting of triethylamine, diazabicycloundecene (DBU), and di-isopropylethylamine.

3. The process according to claim 1, wherein a) is carried out in dichloromethane.

4. The process according to claim 1, wherein a) is carried out in the presence of propanephosphonic acid anhydride.

5. The process according to claim 1, wherein b) is carried out in presence of an oxidizing reagent (+)-(2R,4aS,7S,8aR)-4H-4a, 7-methanooxazirino[3,2-i] [2,1] benzisothiazole, 8,8-dichlorotetrahydro-9,9-dimethyl-3,3-dioxide.

6. The process according to claim 1, wherein b) is carried out in presence of tetrahydrofuran (THF) or diethylether.

7. The process according to claim 1, wherein b) is carried out in presence of sodium-hexamethyldisilazane (NaHMDS).

8. The process according to claim 1, wherein c) is carried out in presence of NaOH.

* * * * *

UNITED STATES PATENT AND TRADEMARK OFFICE
CERTIFICATE OF CORRECTION

PATENT NO. : 12,378,225 B2
APPLICATION NO. : 17/597102
DATED : August 5, 2025
INVENTOR(S) : Timo Heinrich and Jeyaprakashnarayanan Seenisamy Page 1 of 1

It is certified that error appears in the above-identified patent and that said Letters Patent is hereby corrected as shown below:

In the Claims

Column 24, Claim 1, Line 1 currently reads:
"a) reacting 2-oxo-l-(l-(phenylsulfonyl)-H-indol-5-yl)"
And should read:
-a) reacting 2-oxo-1-(1-(phenylsulfonyl)-1H-indol-5-yl)-;

Column 24, Claim 1, Line 10 currently reads:
"difiuorophenyl)methyl]-3-hydroxy-2-oxopyrrolidine-"
And should read:
-difluorophenyl)methyl]-3-hydroxy-2-oxopyrrolidine-;

Column 24, Claim 1, Line 13 currently reads:
"(3S)-1-[ 1-(benzenesulfonyl)-1H-indol-5-yl]-N-[3,"
And should read:
-(3S)-1-[ 1-(benzenesulfonyl)-1H-indol-5-yl]- N-[(3,-;

Column 24, Claim 2, Line 20 currently reads:
"out presence of"
And should read:
-out in presence of-;

Column 24, Claim 5, Line 29 currently reads:
"[2,1]"
And should read:
-[2, 1].-.

Signed and Sealed this
Eleventh Day of November, 2025

John A. Squires
*Director of the United States Patent and Trademark Office*